US009288881B2

(12) United States Patent
Mason

(10) Patent No.: US 9,288,881 B2
(45) Date of Patent: Mar. 15, 2016

(54) CONTROL ARRANGEMENT FOR CONTROLLING AN ATMOSPHERE GENERATING DEVICE

(75) Inventor: Jonathan David Mason, Waalre (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1138 days.

(21) Appl. No.: 13/375,780

(22) PCT Filed: May 26, 2010

(86) PCT No.: PCT/IB2010/052328
§ 371 (c)(1),
(2), (4) Date: Dec. 2, 2011

(87) PCT Pub. No.: WO2010/140081
PCT Pub. Date: Dec. 9, 2010

(65) Prior Publication Data
US 2012/0078401 A1 Mar. 29, 2012

(30) Foreign Application Priority Data

Jun. 2, 2009 (EP) .................................... 09161649

(51) Int. Cl.
*G05B 11/01* (2006.01)
*G05B 15/00* (2006.01)
(Continued)

(52) U.S. Cl.
CPC ............. *H05B 37/0245* (2013.01); *A61L 9/125* (2013.01); *G05B 15/02* (2013.01); *G05B 19/042* (2013.01); *G05B 19/0426* (2013.01); *G06F 3/00* (2013.01); *G06F 3/03* (2013.01); *G06F 3/033* (2013.01)

(58) Field of Classification Search
CPC ............. G06F 3/00; G06F 3/03; G06F 3/033; A61L 9/125; H05B 37/0245; G05B 19/042; G05B 19/0426; G05B 15/02
USPC ....................................................... 700/17, 83
See application file for complete search history.

(56) References Cited

U.S. PATENT DOCUMENTS 7,280,439 B1    10/2007  Shaddox
7,444,187 B2 *  10/2008  Diederiks ............... G06F 3/033
                                                  700/17

(Continued)

FOREIGN PATENT DOCUMENTS

GB        2422448 A    7/2006
JP    2006517721 A     7/2006
(Continued)

OTHER PUBLICATIONS

PCT/AU2006/000917; printed from Internet on May 17, 2015; 29 pages; Cohen.*

(Continued)

*Primary Examiner* — Ronald Hartman, Jr.
(74) *Attorney, Agent, or Firm* — Meenakshy Chakravorty

(57) ABSTRACT

The present invention relates to a control arrangement for controlling an atmosphere generating device, comprising a control device (102) having a control surface (110), and a control object (104, 106) adapted to be freely-positioned onto the control surface, the control object comprising identification means (116), wherein the control device comprises a control unit (114) adapted to identify the control object, to receive relative positioning information from the control surface relating to the positioning of the control object, and to output control data corresponding to the placement information for controlling the atmosphere generating device. By means of the invention it is provided an intuitive user interface in which the user is provided with a flexible solution in which not only repositioning of the control object onto the surface of the control device influence the atmosphere, but also the identity of the control object.

13 Claims, 3 Drawing Sheets

(51) Int. Cl.
*H05B 37/02* (2006.01)
*G06F 3/00* (2006.01)
*G06F 3/03* (2006.01)
*G06F 3/033* (2013.01)
*A61L 9/12* (2006.01)
*G05B 19/042* (2006.01)
*G05B 15/02* (2006.01)

(56) References Cited

U.S. PATENT DOCUMENTS

| | | | |
|---|---|---|---|
| 7,786,889 B2 * | 8/2010 | Van Der Poel | A61L 9/125 340/326 |
| 2003/0011635 A1 | 1/2003 | Hasha et al. | |
| 2003/0057887 A1 | 3/2003 | Dowling et al. | |
| 2008/0203943 A1 | 8/2008 | Baaijens et al. | |
| 2008/0284723 A1 * | 11/2008 | Cohen | 345/156 |
| 2010/0201614 A1 * | 8/2010 | Cohen | 345/156 |

FOREIGN PATENT DOCUMENTS

| | | |
|---|---|---|
| JP | 2007536720 A | 12/2007 |
| WO | 2006038135 A1 | 4/2006 |
| WO | 2006129250 A1 | 12/2006 |
| WO | 2008120127 A1 | 10/2008 |

OTHER PUBLICATIONS

WeatherTank: A Tangible Interface using Weather Metaphors http://web.media.mit.edu/~stefanm/tangible/WeatherTank_short.2001.12.07b.pdf See the higlighted portions of WeatherTank_short.2001.12.07b.pdf.

Sun and Moon Clock ScreenSaver 1.3, http://www.filetransit.com/view.php?id=46806, 2010.

* cited by examiner

CONTROL ARRANGEMENT FOR CONTROLLING AN ATMOSPHERE GENERATING DEVICE

TECHNICAL FIELD

The present invention relates to a control arrangement, specifically to a control arrangement for controlling an atmosphere generating device.

BACKGROUND OF THE INVENTION

Recently, much progress has been made in increasing the brightness of light emitting diodes (LEDs). As a result, LEDs have become sufficiently bright and inexpensive, to serve as a light source in for example lighting arrangements such as lamps with adjustable color. By mixing differently colored LEDs any number of colors can be generated, e.g. white. An adjustable color lighting system is typically constructed by using a number of primary colors, and in one example, the three primaries red, green and blue are used. The color of the generated light is determined by the LEDs that are used, as well as by the mixing ratios. To generate "white", all three LEDs have to be turned on. By using LEDs it is possible to decrease the energy consumption, a requirement which is well in line with the current environmental trend.

As a consequence of having the possibility to provide bright light of different colors, a number of different illumination devices have been proposed where a user is giving the option to change the color to suit the current psychological mood or for creating a specific illumination design. Philips LivingColors is a commercially available example of such an illumination device.

In relation to the Philips LivingColors illumination device, there is provided a user interface in the form of a remote control for allowing the user to change the color and the intensity of light emitted by the illumination device. However, in relation to larger illumination system comprising a plurality of illumination devices there is a desire to provide a more comprehensive user interface that allows for overall control of the different illumination devices for creating and adjusting the common illumination pattern created jointly by the different illumination devices.

An example of such a user interface for controlling light attributes of a lighting interaction system is disclosed in WO 2008/120127 assigned to the applicant and fully incorporated by reference in its entirety. More specifically WO 2008/120127 relates to a user interface comprising a pointer that may be used by a user for pointing to one of a plurality of indicators corresponding to lighting settings relating to for example time of day, description of a natural light condition, season of year, weather, and phase of a moon. Accordingly, by means of the user interface it may be possible to control the lighting interaction system such that a jointly created illumination pattern provided by a plurality of light sources of the lighting interaction system mimicking natural light.

However, even though the lighting interaction system of WO 2008/120127 provides a common user interface for a plurality of light sources, it may be desirable to provide even more intuitively adapted control of such a lighting interaction system, for example related to the feedback provided to the user during operation of the user interface.

SUMMARY OF THE INVENTION

According to an aspect of the invention, the above is at least partly met by a control arrangement for controlling an atmosphere generating device, comprising a control device having a control surface, and a control object adapted to be freely positioned onto the control surface, the control object comprising identification means, wherein the control device comprises a control unit adapted to identify the control object, to receive relative positioning information from the control surface relating to the positioning of the control object, and to output control data corresponding to the placement information for controlling the atmosphere generating device.

The general concept of the present invention is based on the fact that it may be possible to allow for dynamic control of the atmosphere within a space, such as a room, by means of at least an atmosphere generating device being controlled by the control arrangement. The control is according to the invention provided by moving/repositioning an identifiable control object onto a dedicated surface, where the surface comprises means for determine the position and forward the positioning information to the control unit. In turn, the control unit correlates the identity of the control object with the positioning information for as an output providing control data that may be used by the atmosphere generating device for changing its characteristics.

Accordingly, by means of the invention it is provided an intuitive user interface in which the user is provided with a flexible solution in which not only repositioning of the control object onto the surface of the control device influence the atmosphere, but also the identity of the control object. Thus, multiple users may be provided with different control object that for example corresponds to a specific pre-defined atmosphere setting that may be taken into account by the control unit in providing control data to an atmosphere generating device.

In a preferred embodiment the identification means of the control object is at least one of an RFID tag and a magnet. Correspondingly, the control device may be provided with a sensor for determining the identity of the control object, including for example an RFID tag reader or a magnetic reader. It should however be noted that the control object and/or in combination with the control device may comprise different means for providing identification of a specific control object, including for example the positioning of the control object on a small conveyor possibly comprised with the control device, and using the mass of the control object for identification.

Preferably, the control object is a ball and the control surface has at least a groove for receiving the ball. The groove may for example be circular and thus in an exemplary embodiment representing a cyclic progress, including for example the time of the day, the day within a week/month/year and/or seasonal changes (i.e. spring, summer, autumn and winter). Alternatively, the control surface may comprise a plurality of grooves each adapted to receive the ball and/or each adapted to each receive a ball.

In another preferred embodiment the control device further comprises a light source for illuminating the control object, and at least one of the color and the intensity of the light source may depend on the control data provided by the control unit. As a consequence, the control object may change color and/or intensity as the user moves/repositions the control object on the surface. Accordingly, the user may be given a direct feedback as to the changes in atmosphere not only by the feedback provided by actually changing the atmosphere in the space, but also through a direct feedback at the user interface. The light source may be arranged as a backlight "behind" the control surface and illuminate the control object, such as the ball, through the control surface. The control object may for example be of an at least semi-transparent material thus also allowing the light from the light source to be coupled into the control object. Thus, the control object may preferably be arranged in direct contact with the control surface. Preferably, the light source comprises at least a light emitting diode (LED). In an even more preferred embodiment, the light source may for example comprise a combination of at least some of red, green, blue, yellow, magenta and cyan LEDs for creating mixed color lighting.

Alternatively, the control object may comprise a light source, for example comprised within the ball. In such a case the control object may also comprise an intermediate storage unit, such as a battery, for providing power to the light source. The battery may for example be charged inductively, possibly by means of the control device comprising suitable charging means. Additionally, the at least one of the color and the intensity of the light source may also in such a case be controlled wirelessly by corresponding means comprised in the control object and the control device.

The control device may furthermore comprise means for repositioning of the control object, such as an array of electromagnets, according to a predetermined pattern. Accordingly, in an embodiment the control object may comprise a material having magnetic characteristics or that may be influenced by a magnetic field. By providing for the possibility to also repositioning the control object according to a predetermined pattern it is possible to automatically reposition the control object and consequently automatic control of the atmosphere within the space. Additionally, in an embodiment the control unit may include functionality for adaptively changing the predetermined pattern and possibly taking into account a pre-recorded movement pattern of a user using the control arrangement. As such, it may be possible to learn parameters such as for example only changing the atmosphere between predefined settings relating to selected atmosphere.

In an embodiment the predetermined pattern may be adapted to take into account the sun and its path through the sky. Accordingly, the positioning of the control object (e.g. the ball "as the sun") on the control surface (e.g. "the groove as the orbit of the sun") may determine the setting of the atmosphere, e.g. the atmosphere generating device(s) influencing the space. For example, in the morning the ball may glow orange and the atmosphere generating device(s) in the space may provide the feeling of a sunrise. At noon the ball may glow bright yellow and the atmosphere generating device(s) in the space may be bright (or in sequence with the natural light entering the room). In the evening, the ball may glow red and purple to indicate a sunset. During the night, the atmosphere generating device(s) may be turned off, except for the ball, which may glow (possibly dynamically) with a cool white when it will represent the moon for providing an indication as to where to find the control arrangement.

The control arrangement may in the case the predetermined pattern is based on the time of the day be used as a time piece and accordingly changing position and color and/or intensity depending on the current time. In using the control arrangement as a time piece, the control unit may also comprise functionality to e.g. provide wake-up and/or fall asleep functions.

For providing further configuration possibilities the control surface may comprises a display, such as an LCD, OLED or any other suitable display. By using a display it may be possible to also adapt the appearance of the control surface to indicate for the user to which position to move for achieving a specific atmosphere.

Additionally, the control device may further comprise means for wireless communication of the control data to, and from, the atmosphere generating device. Such means may for example include means for allowing light and/or RF transmission of the control data to the atmosphere generating device. As a consequence, the atmosphere generating device may be provided with means for allowing wireless reception of such control data. However, the control device and the atmosphere generating device may connected by wire and the control data may be communicated instead (or also) by wire. A combination of wireless and wired communication may be possible and is within the scope of the invention. Also, the control device may be adapted to receive for example commands relating to the above discussed predetermined patterns, such as for example provided by means of a light control software being executed on an external computer.

In an embodiment of the invention, the control arrangement is provided as a part of an atmosphere generating system further comprising at least an atmosphere generating device. The atmosphere generating device may for example be at least one of a luminaire, a loud speaker, a heater, an air-con, a fragrance generating device. Accordingly, the control arrangement may be adapted to control a combination of different devices to provide a joint influence on the atmosphere in the space.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which.

DETAILED DESCRIPTION

Figure 1A:
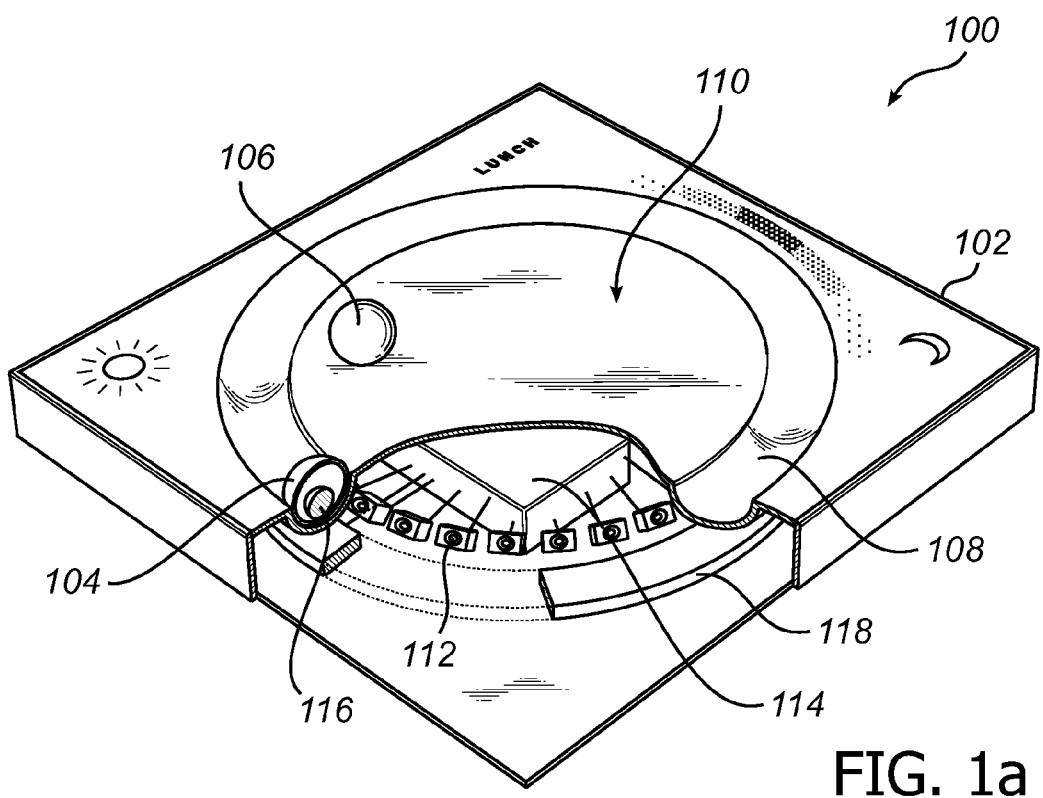
FIGS. 1a and 1b illustrates control arrangements according to currently preferred embodiments of the present invention.

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Referring now to the drawings and to FIG. 1a in particular, there is depicted a perspective view of a control arrangement 100 according to a currently preferred embodiment of the present invention. In the illustrated embodiment, the control arrangement 100 comprises a control device 102 and a first and a second control object, in the form of two balls 104, 106. The first ball 104 is arranged in a groove 108 in a control surface 110 of the control device 102 and the second ball 106 is placed directly on the surface 110. The surface may comprise a display portion (not shown) for adaptively indicate different atmosphere settings that may be controlled according to, e.g. sunny, cloudy, morning feeling, afternoon sun, etc.

In the embodiment of FIG. 1a the control surface 110, or at least a portion of it, is at least semi-transparent. The section of the control surface 110 not comprising a groove may be essentially flat, but may also comprise a plurality of dimples, thus possibly introducing increased friction between the ball 106 and the surface 110. Accordingly, behind the control surface 110 it may be arranged a plurality of light source, such as LEDs 112, that may be adapted to couple light into the balls 104, 106. Thus, the balls 104, 106 preferably also comprise an at least semi-transparent material, such as glass or a plastic material, for out-coupling of the light emitted by the LEDs 112. The LEDs may be of different color for providing light of different color or for mixing light of different color.

The control device 102 further comprises a control unit 114 configured in electrical connection with the control surface 110 for determining a relative position of the balls 104, 106 of one or a plurality of control objects, such as the first and the second ball 104, 106. The control unit may 114 include a microprocessor, microcontroller, programmable digital signal processor or another programmable device. The control unit 114 may also, or instead, include an application specific integrated circuit, a programmable gate array or programmable array logic, a programmable logic device, or a digital signal processor. Where the control unit 114 includes a programmable device such as the microprocessor, microcontroller or programmable digital signal processor mentioned above, the processor may further include computer executable code that controls operation of the programmable device.

Additionally, the balls 104, 106 comprise identification means making different balls distinguishable from each other. Such identification means may for example comprise a magnet 116, an RFID tag, or weights making different balls having distinguishably different weights. For determining the identity of the balls 104, 106, the control device 102 may be equipped with a sensor 118 for sensing for example the magnetic field of the ball 104, 106. The sensor 118 may also be combined with an electromagnet for repositioning the balls 104, 106 according to a predetermined pattern. Such a predetermined pattern may for example include moving the ball 104 around the groove 108 based on the time of the day. As such, a complete revolution may for example represent a complete 24 hour calendar day.

Figure 1B:
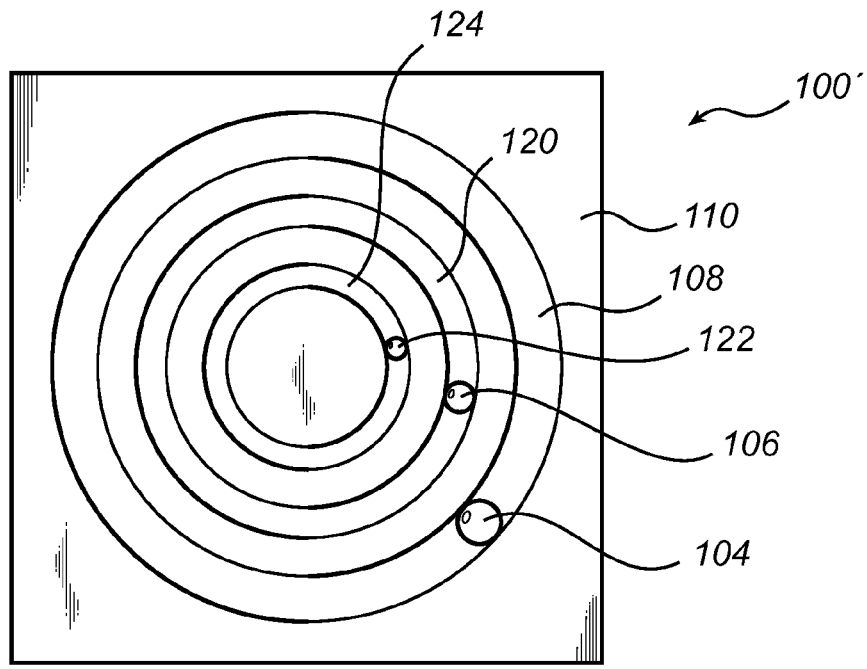
Figure 2:
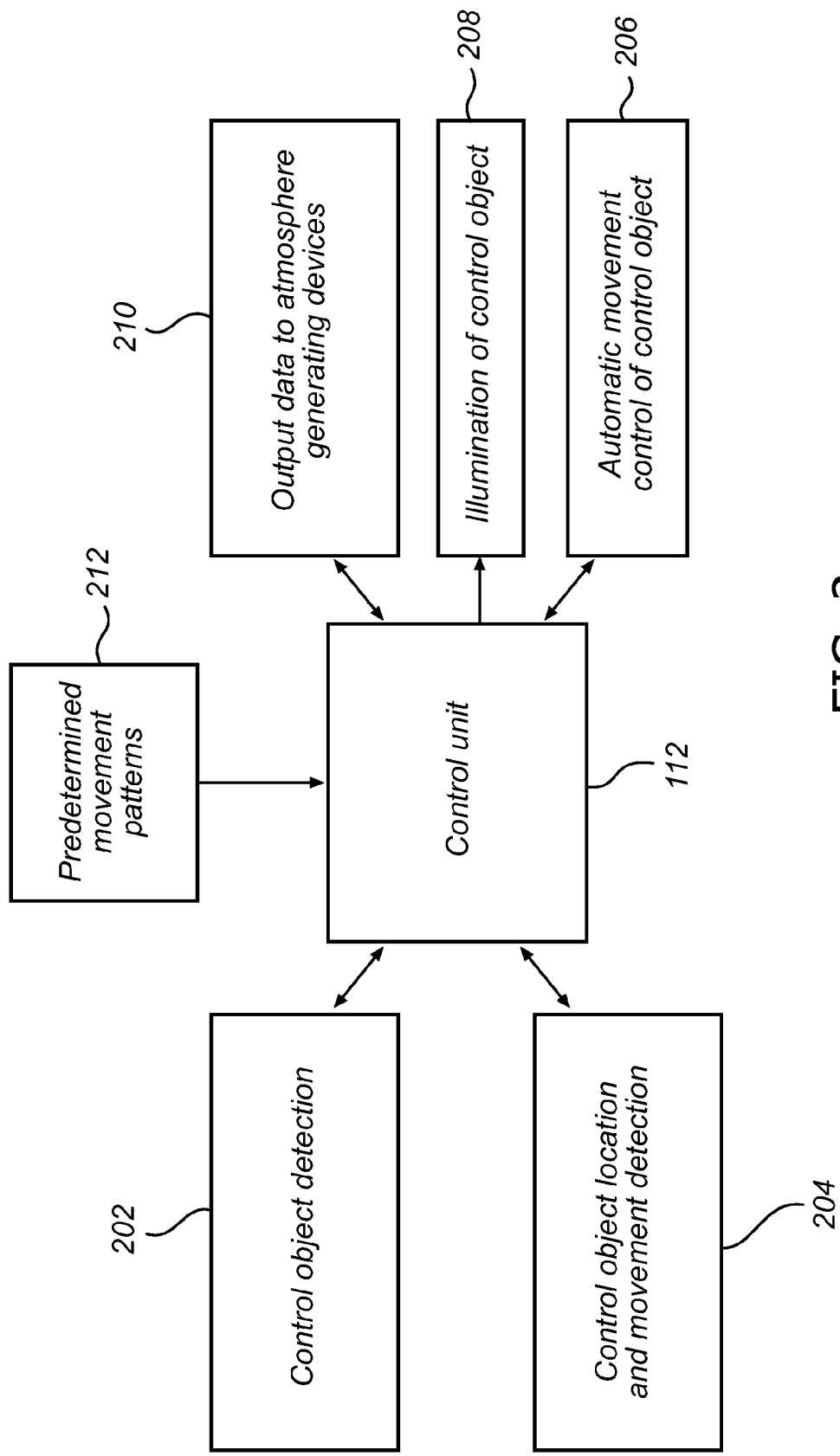
FIG. 2 is a functional block diagram illustrating the control functionality of a control unit comprised with a control arrangement.

In an alternative embodiment of a control arrangement 100', the control surface 110 may comprise a plurality of grooves. Such an embodiment is illustrated in FIG. 1b, where the first ball 104 is positioned in the first groove 108, the second ball is positioned in a second groove 120, and an additional ball 122 is positioned in a third groove 124. In using a plurality of grooves, the individual positioning of one ball in one specific groove may influence the progress of another groove and ball e.g. day scenes (i.e. atmospheres) may take on an essence of for example autumn if for example another groove relating to seasonal changes is comprised. Accordingly, the first groove 108 may represent the time of the day, the second groove 120 may represent the day within a month and the third groove 124 may represent the month within a year, thus including the seasonal changes within a year.

During operation of the control arrangement 102 the control unit 112 provides global control for adjusting one or a plurality of atmosphere generating devices for jointly creating an atmosphere in space such as a room. The functions provided by the control unit 112 may be divided into a plurality of functional blocks, including a detection and identification block 202 where the control unit detects the presence of a control object, such as balls 104, 106, and 122 on the control surface and subsequently determines the identity of the control object. Another functional block 204 includes the functionality for determining the location and movement of the control object onto the control surface 110. Additionally, a functional block 206 for automated movement of the control objects 104, 106 may be provided, for example for controlling the electromagnets 118 according to a predetermined pattern. Further, there is provided a functional block 208 for controlling the illumination of the control object, a functional block 210 for providing control data to one of a plurality of atmosphere generating devices and a functional block 212 for receiving predetermined movement patterns from for example a lighting control software.

Also, the control unit 112 may comprise functionality configured for wireless communication of the control data to, and from, one or a plurality of atmosphere generating devices. The wireless communication functionality may include for example light (e.g. IR) and/or RF transmission of the control data. Also a wired (or combined wireless and wired) connection between the control arrangement 100/101' and the atmosphere generating devices may be included.

Figure 3:
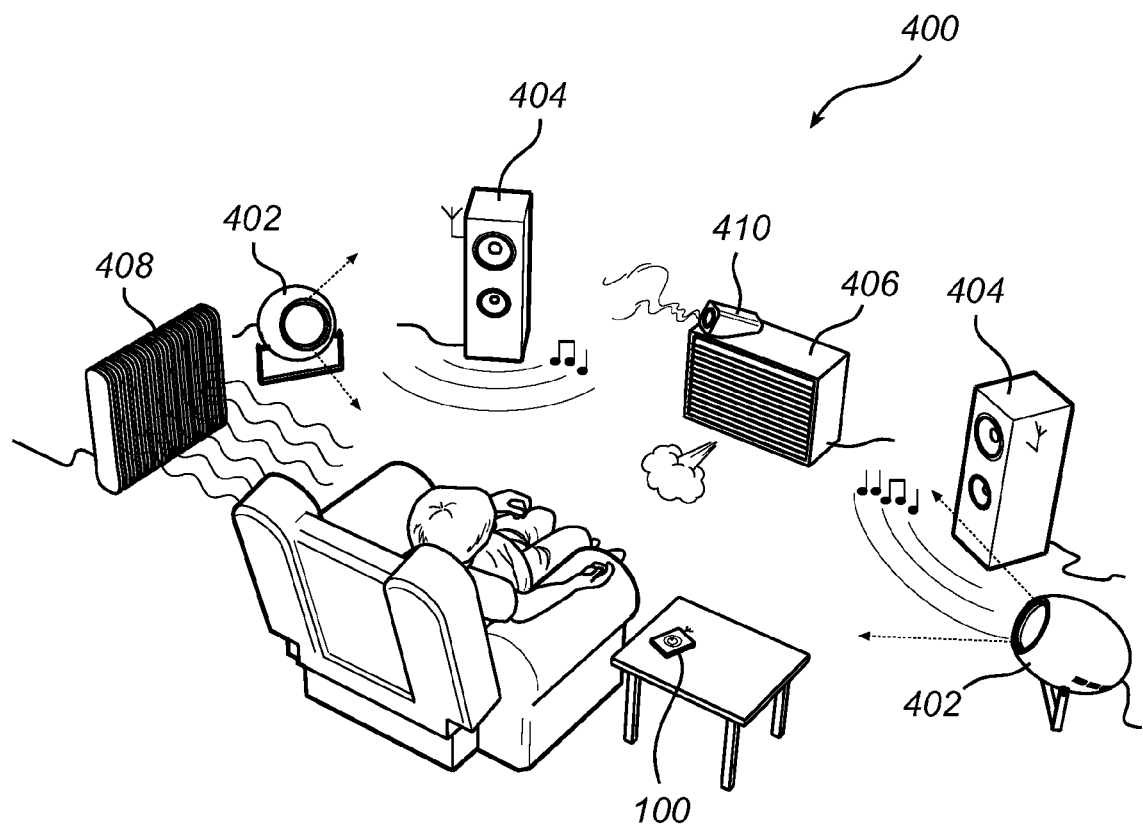
FIG. 3 illustrates an atmosphere generating system comprising a plurality of atmosphere generating devices and a control arrangement according to the invention.

Turning now to FIG. 3, which illustrates an atmosphere generating system 400 comprising a control arrangement 100 according to the invention and a plurality of atmosphere generating devices arranged in a space, such as a room. The atmosphere generating devices includes a pair of luminaires 402, a pair of loud speakers 404, an air-conditioning arrangement 406, a heater 408 and a fragrance generating device 410. Other atmosphere generating devices may of course be included. Each of the atmosphere generating devices are configured to wirelessly receive control data from the control arrangement 100 for providing individual adjustments of the different characteristics that may be provided by the different atmosphere generating devices. For example, the pair of luminaire 404 may be configured to emit light of different color and/or intensity, whereas the fragrance generating device 410 may be configured to generate different fragrances, for example from an atmosphere perspective corresponding to e.g. the beach, a forest, flower, smells of animals or people, etc.

Accordingly, the atmosphere in the space depends not only on light provided by for example a single luminaire, but by joint outputs from different atmosphere generating devices. As an example, the control arrangement 100 may be adapted to monitor the time of the day passively. As such, if a user is working at home or in an hotel room, as it became later in the evening the atmosphere generating device(s) may dim and change color slightly as the 'sunsets' and the user may as a result notice a gradual difference and be remaindered to e.g. stop working or that it is time for dinner. In summary, the present invention relates to a control arrangement for controlling an atmosphere generating device, comprising a control device having a control surface, and a control object adapted to be freely positioned onto the control surface, the control object comprising identification means, wherein the control device comprises a control unit adapted to identify the control object, to receive relative positioning information from the control surface relating to the positioning of the control object, and to output control data corresponding to the placement information for controlling the atmosphere generating device.

By means of the invention it is provided an intuitive user interface in which the user is provided with a flexible solution in which not only repositioning of the control object onto the surface of the control device influence the atmosphere, but also the identity of the control object.

Even though the invention has been described with reference to specific exemplifying embodiments thereof, many different alterations, modifications and the like will become apparent for those skilled in the art. Variations to the disclosed embodiments can be understood and effected by the skilled addressee in practicing the claimed invention, from a study of the drawings, the disclosure, and the appended claims. That is, even though the control arrangement has been described in relation to the combination of one or a plurality of groove and one or a plurality of balls, it may also be possible to adapt the control arrangement in many different ways that falls within the scope of the claims. For example, the groove does not necessarily need to be circular, but a reciprocating linear (vertical or horizontal) arrangement could also be possible. In such a case it may however be necessary to further emphasis on the color of the control object since it will pass through the same position at least twice. Additionally, the ball and the groove could be replaced with arms as on a clock, and the user may select, replace and move arms to show their preference or whether it is in automatic or manual modes. Furthermore, in the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A control arrangement for controlling an atmosphere generating device, comprising:
    a control device having a control surface; and
    a control object positionable onto the control surface, the control object being at least semi-transparent and comprising a light source for illuminating the control object and identification means, wherein the control device comprises a control unit configured to identify the control object, to receive relative positioning information from the control surface relating to the positioning of the control object, and to output control data corresponding to placement information for controlling the atmosphere generating device.

2. The control arrangement according to claim 1, wherein the identification means is at least one of an RFID tag and a magnet.

3. The control arrangement according to claim 1, wherein the control device further comprises a light source for illuminating the control object.

4. The control arrangement according to claim 3, wherein at least one of color and intensity of the light source depends on the control data provided by the control unit.

5. The control arrangement according to claim 1, wherein the control object comprises an intermediate storage unit.

6. The control arrangement according to claim 1, wherein the control object is a ball and the control surface has at least a groove for receiving the ball.

7. The control arrangement according to claim 1, wherein the control device comprises means for repositioning of the control object according to a predetermined pattern.

8. The control arrangement according to claim 7, wherein the means for repositioning of the control object comprises an array of electromagnets.

9. The control arrangement according to claim 7, wherein the predetermined pattern is depending on the time of the day.

10. The control arrangement according to claim 1, wherein the control surface comprises a display.

11. The control arrangement according to claim 1, wherein the control device further comprises means for wireless communication of the control data to the atmosphere generating device.

12. An atmosphere generating system, comprising an atmosphere generating device and a control arrangement according to claim 1.

13. The atmosphere generating system according to claim 12, wherein the atmosphere generating device is at least one of a luminaire, a loud speaker, a heater, an air-conditioning unit, and a fragrance generating device.

* * * * *